United States Patent [19]

Gullberg et al.

[11] Patent Number: 4,703,424
[45] Date of Patent: Oct. 27, 1987

[54] METHOD AND MEANS OF CORRECTING FOR A SHIFT IN THE CENTER OF ROTATION OF A ROTATING FAN BEAM CT SYSTEM

[75] Inventors: Grant T. Gullberg, Waukesha; Carl R. Crawford, Milwaukee, both of Wis.

[73] Assignee: General Electric Company, Waukesha, Wis.

[21] Appl. No.: 688,486

[22] Filed: Jan. 3, 1985

[51] Int. Cl.⁴ .............................................. G06F 15/42
[52] U.S. Cl. .................................... 364/414; 378/901; 364/571; 364/581
[58] Field of Search ....................... 364/414, 571, 581; 378/4.62, 901

[56] References Cited

PUBLICATIONS

Michael J. Dennis et al., "Preprocessing X-Ray Transmission Data in CT Scanning", *Optical Scanning*, vol. 16, No. 1, pp. 6-10, Jan.-Feb. 1977.
Franklin J. Weinstein, "Formation of Images Using Fan-Beam Scanning and Noncircular Source Motion", *J. Opt. Soc. Am.*, vol. 70, No. 8, pp. 931-935, Aug. 1980.
C. R. Crawford and A. C. Kak, "Multipath Artifacts in Ultrasonic Transmission Tomography", School of Electrical Engineering, Purdue University, Research Report TR-EE 81-43, pp. 146-161, Dec. 1981.
M. F. Kijewski and P. F. Judy, "The Effects of Misregistration of the Projections on Spatial Resolution of CT Scanners", *Medical Physics*, vol. 10, No. 2, pp. 169-175, Mar./Apr. 1983.

*Primary Examiner*—Jerry Smith
*Assistant Examiner*—Gail O. Hayes
*Attorney, Agent, or Firm*—Leydig, Voit & Mayer

[57] ABSTRACT

Method and means for determining and compensating for a shift in the center of rotation of a fan beam CT reconstruction apparatus. Known reconstruction algorithms for fan beam computed tomography are based on the assumption that the center of rotation of the source or detector is on the midline of the fan. In certain cases due, for example, to machine inaccuracies, the center of rotation can be shifted from the assumed center, and such shift can cause artifacts in the reconstruction. The present invention provides a procedure for estimating the magnitude of the shift and also accommodates for the shift by applying a series of weighting factors to the projection information which are dependent on the magnitude of the shift. The weighted projections are then processed by the usual convolution operation, and the convolved projection sets back projected using a geometry modified to account for the shift. Efficiencies are achieved in that all projection sets can be weighted and convolved before back projection, and existing back projection hardware or software can be used to map the modified projection sets into the pixelized image space.

17 Claims, 8 Drawing Figures

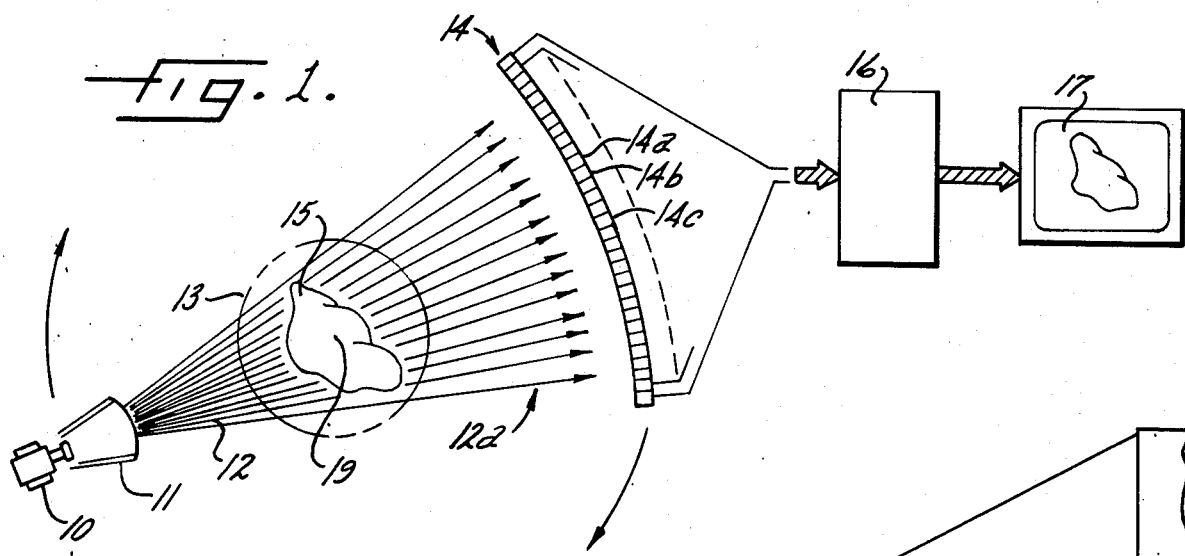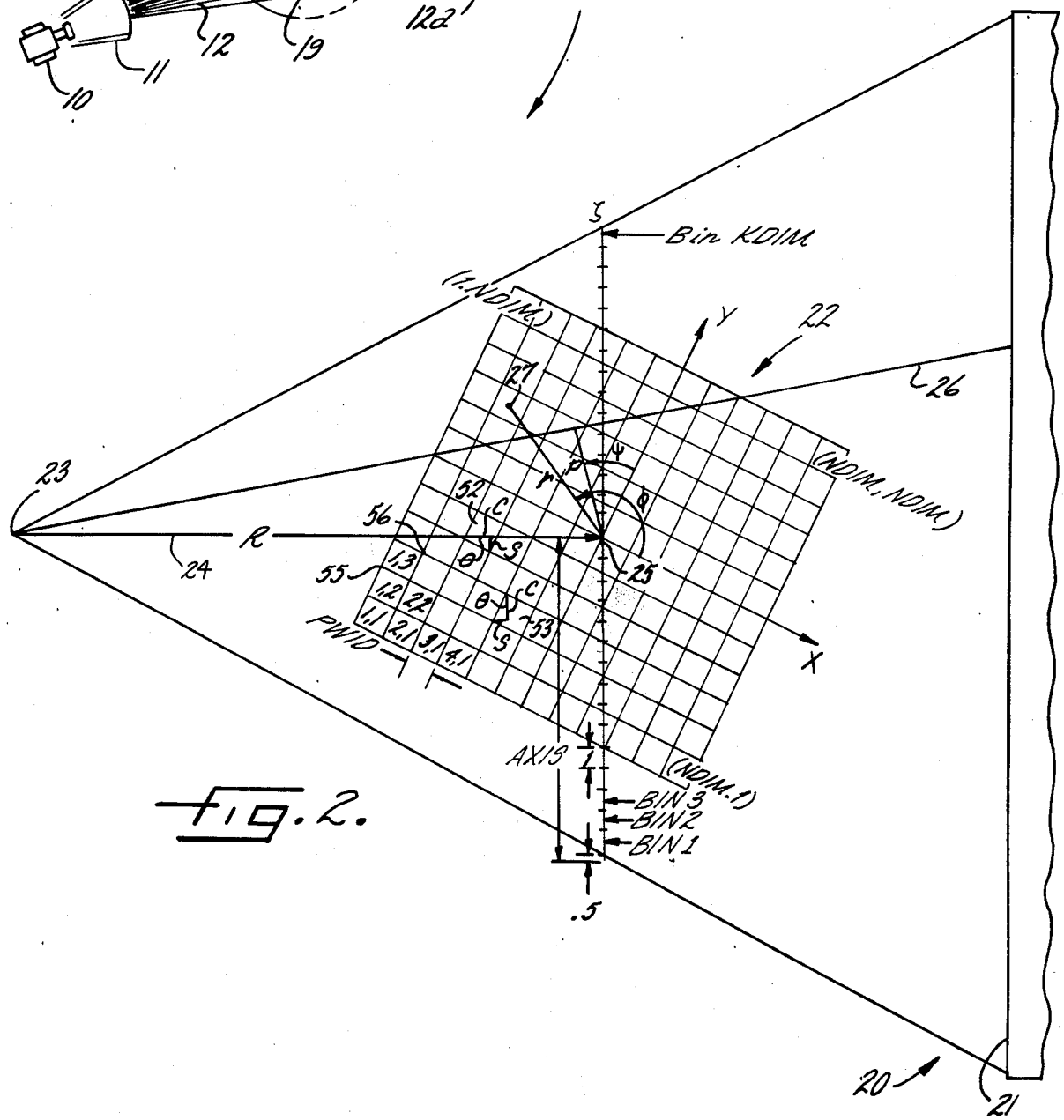

METHOD AND MEANS OF CORRECTING FOR A SHIFT IN THE CENTER OF ROTATION OF A ROTATING FAN BEAM CT SYSTEM

BACKGROUND OF THE INVENTION

1. Field of the Invention

This invention relates to computed tomography, and more particularly to fan beam reconstruction techniques.

2. Discussion of the Prior Art

Computed tomography includes the fields of transmission computed tomography and emission computed tomography. In one form of fan beam transmission computed tomography, an X-ray source and a multi-channel detector are fixed with respect to each other and mounted for rotation on a gantry on opposite sides of a patient aperture. During the course of a scan, a number of projections are taken which are later convolved and back projected to produce a pixelized image representing the linear attenuation coefficients of the slice of the body through which the radiation had passed. The geometry of the system is such that the center of rotation of the source-detector assembly is intended to lie on the midline of the fan beam, on a line from the focal point of the source to a predetermined point on the detector.

In emission computed tomography, gamma emitting substances are ingested or injected into the body, following which the body is scanned to detect the concentration and distribution of the radioactive sources by taking projections at a plurality of angles around the body. An example of fan beam emission computed tomography is the rotating gamma camera used with a converging collimator. The collimator is intended to converge at a focal point, and the center of rotation of the collimater and gamma camera is intended to lie on the midline of the fan beam, on a line joining the focal point to a predetermined point on the detector.

The fan beam reconstruction algorithms in use are based on the assumption that the center of rotation of the system is as described above, that is, colinear with a line joining the focal point onto a known point on the detector. When the actual center of rotation is shifted from the midline of the fan, the effect will be artifacts in the reconstruction because the assumptions underlying the algorithm have not been met. In the parallel beam case, it is possible to simply shift the projections prior to processing in order to account for the new center of rotation. However, the fan beam case cannot be corrected by a simple shift, unless of course one rebins the fan beam projections into parallel beam projection sets. Rebinning, however, is considered to be computationally expensive and degrades resolution.

One of the factors which must be accounted for in true fan beam reconstruction algorithms is the diverging nature of the fan beam itself. The normal form of the Radon inversion relationship, on which many reconstruction techniques depend, assumes parallel beam geometry. When fan beam projections are reconstructed, geometric factors are required which account for the relationship between the parallel rays and the diverging rays. That relationship is typically accounted for in or just prior to the convolution operation as well as in the back projection operation which must map the data according to the geometry of the system. However when the center of rotation of the system is shifted, the system geometry is altered, and the standard pre-convolution and back projection factors are no longer directly applicable.

Typically in a transmission CT system as manufactured, the center of rotation will be in its expected location because the gantries of transmission CT systems, which include the X-ray source and detector array, can be constructed with great precision. If the geometry shifts over time, due to mechanical wear or the like, it is a relatively simple task to make measurements during the course of a scan to determine the magnitude of the shift. By way of analogy, in emission CT the detector, including its converging collimator array, cannot be manufactured with comparable precision and thus a shift in geometry including the location of the center of rotation is to be expected. In parallel hole (i.e., parallel beam) systems it is relatively easy to take calibrating measurements to determine the magnitude of the shift. However, up to now there has not been an easy way to accurately measure the magnitude of the shift in a converging collimator (i.e., fan beam) emission CT system.

SUMMARY OF THE INVENTION

In view of the foregoing, it is a general aim of the present invention to determine the magnitude of and to compensate for shifts in the center of rotation of fan beam computed tomographic systems in such a way as to allow the use of convolutional back projection reconstruction techniques.

More particularly, it is an object of the present invention to weight the fan beam projection sets to account for the shift so that standard convolution and back projection techniques can be used on the weighted sets to reconstruct the image.

A further object is to provide a procedure for estimating the shifts in the fan beam reconstruction geometry so that such shifts can accurately be accounted for in the reconstruction operation.

BRIEF DESCRIPTION OF THE DRAWINGS

Other objects and advantages will become apparent from the following detailed description when taken in conjunction with the drawings, in which:

FIG. 1 is a diagram schematically illustrating a fan beam computed tomography system;

FIG. 2 is a diagram illustrating a fan beam CT geometry and shows the relationship between bins in projection space and pixels in image space;

DESCRIPTION OF THE PREFERRED EMBODIMENTS

Figure 3:
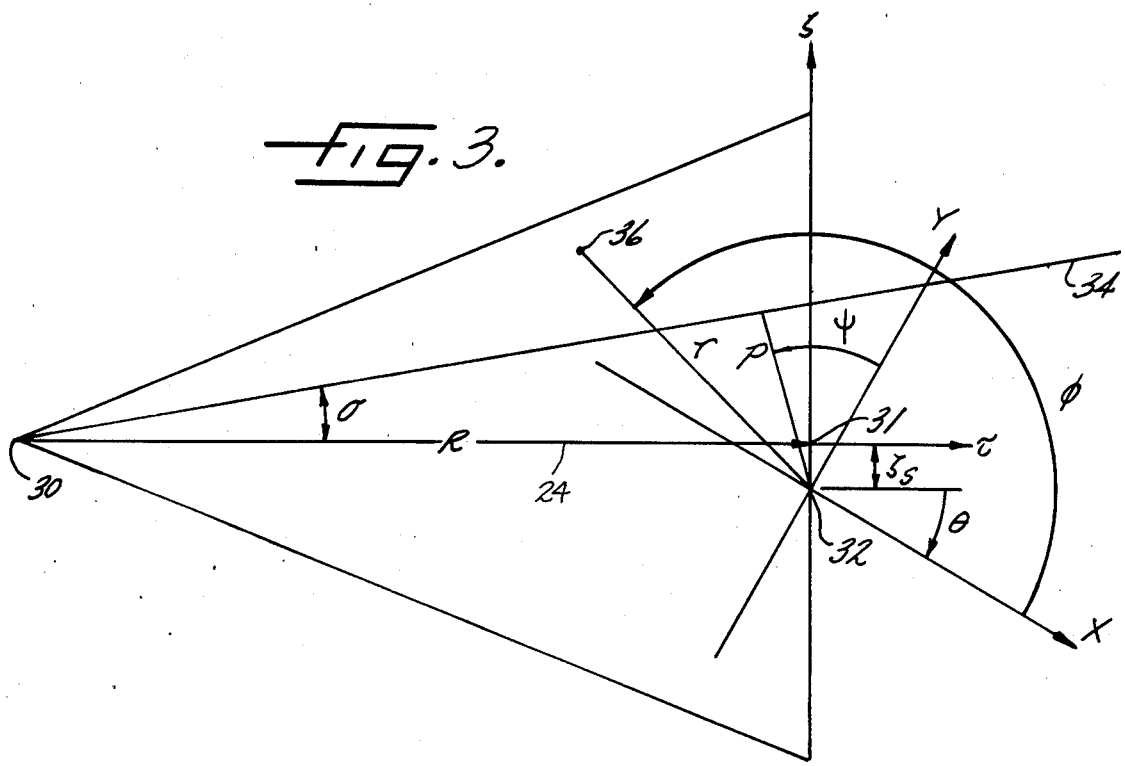
FIG. 3 is a diagram illustrating a shift in the center of rotation for a flat detector fan beam CT system.

While the invention will be described in connection with certain preferred embodiments, there is no intent to limit it to those embodiments. On the contrary, the intent is to cover all alternatives, modifications and equivalents included within the spirit and scope of the invention as defined by the appended claims.

Turning now to the drawings, FIG. 1 schematically illustrates the major elements of a transmission CT scanner. The scanner includes a source of penetrating radiation 10, typically an X-ray tube. The radiation produced by the X-ray tube 10 is collimated at 11 to produce a thin fan beam of radiation 12 which is projected through a patient aperture 13 toward an X-ray detector array 14. A body to be examined, such as a patient 15, is positioned within the patient aperture 13 in the path of the fan beam of X-rays 12 such that the beam passing through the body is attenuated in dependence on the density of the objects encountered. As a result, each detector cell 14a, 14b, 14c, etc. produces an electrical signal which is dependent on the intensity of the radiation received within the cell. A set of such readings is called a projection, and a series of projections are taken as the source and detector rotate about the body. The readings making up each projection are digitized and fed to a reconstruction computer 16 which can use one of a number of available algorithms to produce the image of the cross section traversed by the fan beam. The image can be displayed on a monitor 17, or alternatively, can be used to create a film for further study by a diagnostician. It will be appreciated that in the illustrated example, the source 10 and detector 14 are mounted in a gantry opposite each other for rotation about a point 19 within the patient aperture. Alternatively, in fixed detector systems the detector ring encircles the patient aperture and only the source rotates. In both cases, the fan beam reconstruction algorithms in use assume that the center of rotation 19 falls on a ray which bisects the fan.

The geometry of a fan beam emission CT system can be considered similar to the transmission CT system illustrated in FIG. 1. The emission system, however, has no X-ray source 10 or source collimator 11. Instead, radionucleids within the body 15 emit radiation which is sensed by a rotating detetctor 14, usually in the form of a rotating gamma camera. Usually, the detector face is a flat crystal as illustrated at 21 in FIG. 2 rather than the curved detector of FIG. 1. Interposed between the gamma camera and the patient aperture is a converging collimator which focuses the detector to a focal spot at the opposite side of the patient aperture (see focal spot 23 of FIG. 2) and divides the fan into a plurality of beams. Typically, the collimator is in the form of a plurality of tubes affixed together in a honeycomb like array. One end of each tube is separated from the crystal face 21 by a small distance and the other end aimed at the focal spot 23 such that radiation is received along rays like rays 12a illustrated in FIG. 1. Of course, the tubes terminate short of the patient aperture 13 to form a truncated fan shaped array. Because the crystal face has significant extent in the direction perpendicular to the scan plane, the collimator is usually configured to simultaneously scan multiple transaxial slices. In effect, the truncated fan shaped arrangement just described is duplicated in additional planes parallel to the surface of the paper in FIG. 2 so that a plurality of transaxial slices can be scanned in a single rotation of the detector assembly. As in the transmission case, the detector with its associated collimators is rotated about the center 19 (FIG. 1) to produce a plurality of projections which are digitized, then fed to a reconstruction computer 16 for producing an image of radionucleide concentrations within the body, for display on a monitor 17.

While the mechanics for taking the projections in the above-described exemplary equipment can and do vary, the common thread binding all the systems is the creation of a projection space and the taking of a plurality of projections at a plurality of angles around the projection space. Conventional reconstruction algorithms assume that the projections are all intended to be centered at a center of rotation in the projection space which lies on the midline of the fan. In the curved detector case, the midline is defined as the line which bisects the fan. For the flat detector case, the midline is defined as the projection of the focal point onto the detector, i.e., on a ray through the apex of the fan and normal to the detector. It will be appreciated that the projection in the flat detector case need not exactly bisect the fan.

With respect to exemplary equipment configurations, in third generation CT the source and detector are mounted opposite each other in a gantry for rotation about the center point. In fourth generation CT, the detector is fixed and only the source within the gantry rotates about the center. In the gantries used for emission CT, most often the detector (with its associated collimator rotates about the center of rotation. However, there are emission CT systems in which a plurality of gamma cameras or detectors are mounted around the projection space and only the collimator rotates. In all cases, however, the projection algorithms used to date have assumed that the center of the projection space is the center of rotation of the rotating elements. When the actual center of rotation is shifted, conventional algorithms will create artifacts.

There are a number of conditions which can cause a shift in the center of rotation of a fan beam reconstruction system. In both transmission and emission computed tomography, mechanical wear or stress on the rotating elements can, over time, cause a shift in the center of rotation. In emission computed tomography, the shift may be introduced by inaccuracies in manufacturing the collimator itself. In manufacturing the honeycombed array described above, it is difficult to precisely focus the tubes on the focal spot and at the same time assure the proper geometry with respect to the center of rotation. As a result, the collimator is often configured with an inherent shift between its expected center of rotation, usually the middle of the fan beam, and its actual center of rotation.

Turning again to FIG. 2, it is recalled that the detector 20 is typically a gamma camera having a crystal face 21 and interposed collimators directed through the patient aperture toward the focal spot 23 for each transaxial slice, and aimed to form a fan (for each slice). The apex 23 of the fan and its swath are indicated in FIG. 2. The image space is represented by the pixelized area 22 which can be conceptualized as disposed between the focal spot and the detector/collimator arrangement. In the actual scanning apparatus, the image space is occupied by the body being scanned from which a set of projections is formed. The geometry of FIG. 2 relates the image space to the projections which are collected by the detectors, and after processing, are mapped into the image space to form the reconstructed image.

With respect to the geometry, it is seen that the image space is based on an xy-coordinate system with the origin located at the center of rotation 25 of the system, a fixed distance R from the focal point. The figure illustrates a square pixel array with each pixel of width PWID (measured in units of projection bin width implying that the architecture has been scaled so that distance between adjacent detector bins is unity), having an $(x_i, y_j)$ coordinate with i and j ranging from 1 through NDIM where NDIM is the index of the last element of a row or column of the display as clearly indicated in FIG. 2. The single projection illustrated in FIG. 2 is taken at an angle $\theta$ with respect to the xy-coordinate system.

In a system involving parallel beam geometry, all rays in the projection would be parallel to the center ray 24, simplifying the reconstruction process. However, in the fan beam case illustrated in FIG. 2, the rays diverge from the focal point 23 in a fan shaped swath toward the detector. Taking ray 26 as exemplary, it can be identified in coordinates for parallel beam geometry by the normal $\rho$ drawn from the origin to the ray and the angle $\psi$ formed between the coordinate system and $\rho$. Similarly, any arbitrary point in the reconstruction space, such as point 27, can be identified by its polar coordinates $(r,\phi)$.

In order to simpify the reconstruction process in a true fan beam system, it is desirable to define yet another coordinate system based on the $\xi$ axis which, as shown in FIG. 2, is normal to central ray 24 and intersects the center of rotation. The $\xi$ axis defines a set of projection bins 1 through KDIM, where KDIM is the last bin as shown in FIG. 2, of unit width whose projection information is derived from the detector cells in accordance with the diverging geometry of the fan. Any ray in the fan can be identified by the coordinates $(\xi,\theta)$. Thus, a fan beam projection can be identified by $p(\xi,\theta)$.

As noted previously, when the coordinates of the projections are remapped from parallel beam to account for the diverging nature of the fan beam, the projection bins must be scaled with a geometric factor. More particularly, examining the geometry shown in FIG. 2, it can be shown that $$\frac{\rho}{R} = \frac{\zeta}{\sqrt{R^2 + \zeta^2}}. \quad (1)$$

Rearranging, and relating the differential $d\rho$ to the differential $d\xi$ yields:

$$d\rho = \frac{R^3}{(R^2 + \zeta^2)^{3/2}} d\zeta \quad (2)$$

Thus, a unit change of $\rho$ does not yield a unit change of $\xi$, but a change weighted by the factor indicated in expression 2. In fan beam reconstruction algorithms, the projections are appropriately weighted to take account of this geometric factor. However, when the center of rotation of the system is shifted the weighting factors are no longer valid and use of the conventional reconstruction procedures will generate artifacts.

Attention will now be directed to the modification of the reconstruction process due to the shift in the center of rotation and to determination of a procedure to accommodate the shift while still allowing use of standard convolutional back projection reconstruction techniques. The following explanation considers the continuous analytical solution at the outset. This is given to supply the theory and mathematical background underlying the invention. Following the theory, there is described the manner in which the resulting corrections are implemented in the discrete sampled data environment normally employed in digitally implemented reconstruction techniques. Finally, a method is described for estimating the magnitude of the shift and other relevant fan beam parameters.

Turning now to FIG. 3, there is shown the geometry for a fan beam flat detector CT system in which the center of rotation is shifted. More particularly, there is shown central ray 24 emanating from the focal point 30 and normal to the detector (not shown), intersecting the $\xi$ axis at a point 31 assumed by conventional fan beam algorithms to be the center of the coordinate system $(\tau,\xi)$. The distance R is that measured between the focal spot 30 and the point 31. The actual center of rotation is shown at 32 which is the origin of the rotating xy coordinate system, and is displaced along the $\xi$ axis by a fixed amount $\xi_s$ representing the shift. A typical ray 34 within the fan is shown as having parallel beam projection coordinates $(\rho,\psi)$. Similarly, any arbitrary point 36 within the reconstructed image can be denoted by its polar coordinates $(r, \phi)$.

It is well known that for parallel beam geometry, the Radon inversion relationship can be expressed as:

$$f(r,\phi) = \frac{1}{4\pi^2} \int_0^{2\pi} \int_{-\infty}^{\infty} \left[ -\frac{1}{t} \right] \frac{\partial}{\partial \rho} p(\rho,\psi) d\rho d\psi \quad (3)$$

where $t = \rho - r \sin(\phi - \psi)$.

Integrating by parts and using Cauchy's principal value, expression 3 can be rewritten as:

$$f(r,\phi) = \frac{1}{4\pi^2} \int_0^{2\pi} \lim_{\epsilon \to 0} \int_{-\infty}^{\infty} F_\epsilon(t) p(\rho,\psi) d\rho d\psi \quad (4)$$

$$F_\epsilon(t) = \begin{cases} 1/\epsilon^2 & \text{for } |t| < \epsilon \\ -1/t^2 & \text{for } |t| \geq \epsilon \end{cases} \quad (5)$$

Expressions 4 and 5 indicate that in the parallel beam case, the function at any arbitrary point $f(r,\phi)$ can be determined by the projection information $p(\rho,\psi)$ as modified by a filter function $F_\epsilon(t)$.

In order to modify the expression to account for the fan beam coordinate system shown in FIG. 3, the following transformation of coordinates is utilized in order to equate the parallel beam projections $p(\rho,\psi)$ to the fan beam projections $p(\xi,\theta)$:

$$\rho = \frac{R(\zeta - \zeta_s)}{\sqrt{R^2 + \zeta^2}}, \quad \psi = \theta + \tan^{-1}(\zeta/R). \quad (6)$$

The transformation is based on trignometric relationships similar to those used in connection with expression 1 in which the similar right triangles can be identified as those having the common angle $\sigma$. It will be appreciated that the transformation of coordinates takes the shift into effect. The Jacobian, which rescales the space from parallel projection coordinates to fan beam projection coordinates for the aforementioned transformation is:

$$J(\zeta,\theta) = \frac{R^3 + R\zeta\zeta_s}{(R^2 + \zeta^2)^{3/2}}. \qquad (7)$$

Using the transformation of coordinates, it is possible to rewrite Radon's inversion relationship (expression 4), in terms of the fan beam coordinates $(\xi,\theta)$, as follows:

$$f(r,\phi) = \frac{1}{4\pi^2} \int_0^{2\pi} g(r,\phi,\theta)d\theta \qquad (8)$$

$$g(r,\phi,\theta) = \lim_{\epsilon \to 0} \int F_\epsilon(t)J(\zeta,\theta)p(\zeta,\theta)d\zeta \qquad (9)$$

where t in expression 3 is now a function of $(\xi,\theta)$ and the point $(r,\phi)$ as given by the transformation.

As is known, expression 8 can be considered equivalent to a back projection operation for a fixed point $(r,\phi)$. In normal fan beam systems or in parallel beam systems, the individual projection sets are convolved with a filter function prior to back projection. Thus, if the function $g(r,\phi,\theta)$ can be expressed as a convolution with respect to the variable $\xi$, it may be possible to use convolutional back projection approach while accommodating the shifted center of rotation.

In order to formulate the expression for $g(r,\phi,\theta)$ in terms of a convolution, we have first transformed the expression for t to the fan beam coordinate system using the transformation set out in expression 6:

$$t = \frac{R(\zeta - \zeta_s)}{\sqrt{R^2 + \zeta^2}} - r\sin(\phi - \theta - \tan^{-1}(\zeta/R)). \qquad (10)$$

Figure 4:
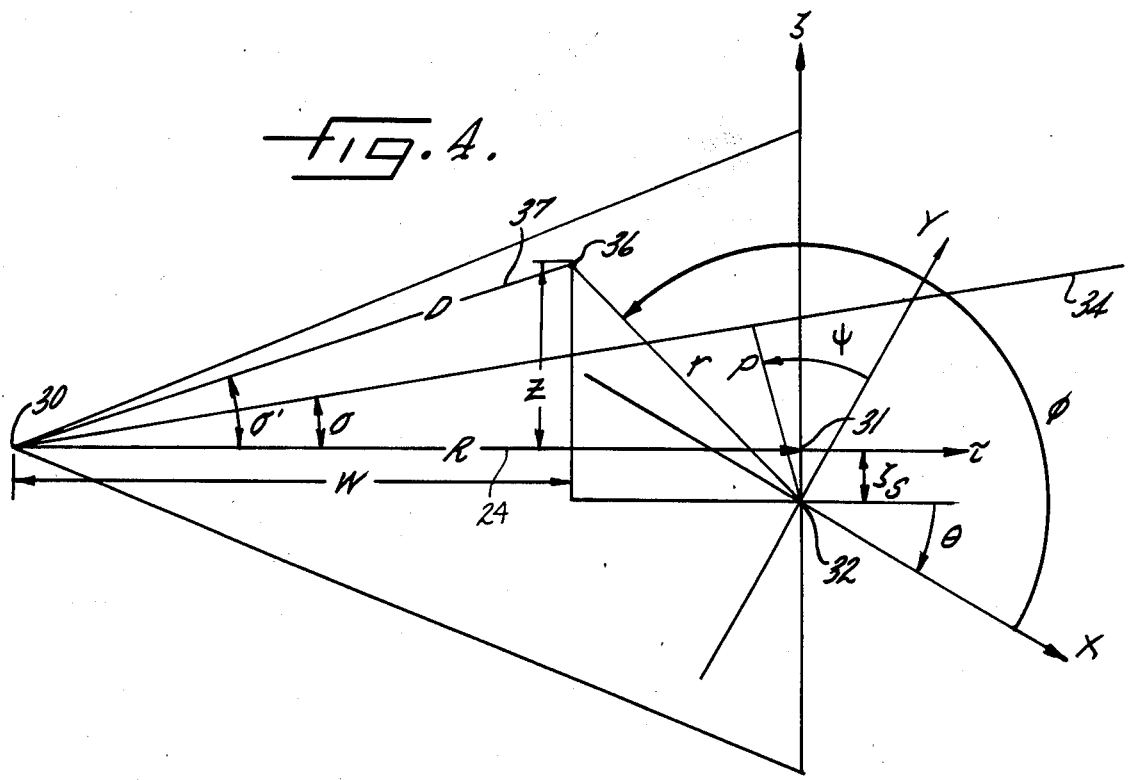
FIG. 4 is similar to FIG. 3 and shows additional geometric relationships in the system of FIG. 3.

It is possible to reformulate expression 10 according to the following:

$$t = D\cos\sigma'\sin\sigma - D\sin\sigma'\cos\sigma = D\sin(\sigma - \sigma') \qquad (11)$$

if one is to define the $\sin\sigma'$, $\cos\sigma'$ and D in accordance with the additional coordinates set out in FIG. 4.

Turning now to FIG. 4, which incorporates the whole of FIG. 3 plus additional information, we can formulate additional variables and coefficients useful in reducing the expression for t to a more suitable form. First of all, it is seen that the angle $\sigma$ is defined between the normal ray R and the ray 34 having parallel projection coordinates $(\rho,\psi)$. Relationships for $\sigma$ can be defined as follows:

$$\sin\sigma = \frac{\zeta}{\sqrt{\zeta^2 + R^2}}, \quad \cos\sigma = \frac{R}{\sqrt{\zeta^2 + R^2}}. \qquad (12)$$

Similarly, an angle $\sigma'$ can be defined between the normal ray R and a ray 37 passing through the point 36 having polar coordinates $(r,\phi)$ as follows:

$$\sin\sigma' = Z/D = (r\sin(\phi-\theta) + \zeta_s)/D,$$

$$\cos\sigma = W/D = (R + r\cos(\phi-\theta))/D. \qquad (13)$$

Finally, squaring the $\sin\sigma'$ and $\cos\sigma'$ expressions set out at 13 and setting their sum equal to 1 yields the following expression for D:

$$D^2 = R^2 + r^2 + \zeta_s^2 + 2r[\zeta_s\sin(\phi-\theta) + R\cos(\phi-\theta)]. \qquad (14)$$

Using the definition of t set out in expression 11, and substituting that value into $g(r,\phi,\theta)$ of expression 9 yields:

$$g(r,\phi,\theta) = \lim_{\epsilon \to 0} \int F_\epsilon(D\sin(\sigma - \sigma'))J(\zeta,\theta)p(\zeta,\theta)d\zeta. \qquad (15)$$

In further reducing the expression for $g(r,\phi,\theta)$ to a coordinate system compatible with the shifted center fan beam geometry, it is useful to manipulate the filter function $F_\epsilon(t)$ set out in equation 5

$$F_\epsilon(t) = \begin{cases} 1/\epsilon^2 & \text{for } |t| < \epsilon \\ -1/t^2 & \text{for } |t| \geq \epsilon \end{cases} \qquad (5)$$

Figure 5:
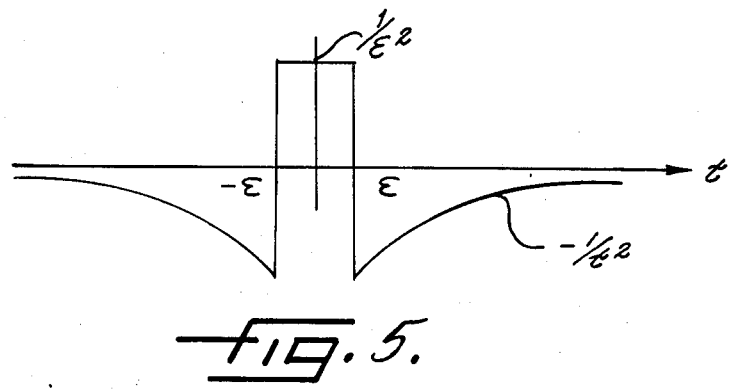
FIG. 5 is a diagram illustrating a filter function for use in the convolution operation for the ideal case of continuous sampling.

The filter function expressed in equation 5 is illustrated in FIG. 5, having a finite value $1/\epsilon^2$ for values of t near zero, and following the curve $-1/t^2$ for values of $|t| \geq \epsilon$. A similar filter function $F_\epsilon(Ct)$ can be defined as follows:

$$F_\epsilon(Ct) = \begin{cases} \dfrac{1}{\epsilon^2} & \text{for } |Ct| < \epsilon \\ \dfrac{-1}{C^2 t^2} & \text{for } |Ct| \geq \epsilon \end{cases} \qquad (16)$$

or:

$$F_\epsilon(Ct) = \frac{1}{C^2}\begin{cases} \dfrac{C^2}{\epsilon^2} & \text{for } |t| < \epsilon/C \\ -\dfrac{1}{t^2} & \text{for } |t| \geq \epsilon/C \end{cases} \qquad (17)$$

Thus, $$F_\epsilon(Ct) = \frac{1}{C^2} F_{\epsilon/C}(t) \qquad (18)$$

where in the limit as $\epsilon \to 0$ the fraction $\epsilon/C$ can be replaced by $\epsilon$. As a result, the expression $g(r,\phi,\theta)$ can now be written as:

$$g(r,\phi,\theta) = \frac{1}{D^2} \lim_{\epsilon \to 0} \int F_\epsilon(\sin(\sigma - \sigma'))J(\zeta,\theta)p(\zeta,\theta)d\zeta. \qquad (19)$$

In order to evaluate the expression $g(r,\phi,\theta)$ as a convolution, it would be useful to further modify the $\sin(\sigma - \sigma')$ expression to produce a form in terms of $(\xi - \xi')$ in the argument of $F_\epsilon$ where $\xi'$ is in terms of the coorindates $(r,\phi)$. Referring again to FIG. 4, it is seen that $\xi = R\tan\sigma$, that is the intersection of the ray 34 with the $\xi$ axis. Similarly, we choose to define $\xi'$ as $R\tan\sigma'$, that is, the intersection of the ray 37 with the $\xi$ axis. Accordingly:

$$\sin\sigma' = \frac{\zeta'}{\sqrt{R^2 + \zeta'^2}} \quad \cos\sigma' = \frac{R}{\sqrt{R^2 + \zeta'^2}}. \qquad (20)$$

Using expressions 20 and 12:

$$\sin(\sigma - \sigma') = (\zeta - \zeta')\frac{R}{\sqrt{R^2 + \zeta^2}\sqrt{R^2 + \zeta'^2}}. \qquad (21)$$

Having thus expressed $\sin(\sigma - \sigma')$ in terms of the desired coordinates $(\xi - \xi')$ and a factor similar in form to C in expression 18, it is possible to rewrite equation 19 as:

$$g(r,\phi,\theta) = \frac{R^2 + \zeta'^2}{R^2 D^2} \lim_{\epsilon \to 0} \int (R^2 + \zeta^2) F_\epsilon(\zeta - \zeta') J(\zeta,\theta) p(\zeta,\theta) d\zeta. \quad (22)$$

Substituting $J(\xi,\theta)$ from expression 7 yields:

$$g(r,\phi,\theta) = \frac{R^2 + \zeta'^2}{RD^2} \lim_{\epsilon \to 0} \int F_\epsilon(\zeta - \zeta') p(\zeta,\theta) \frac{R^2 + \zeta \zeta_s}{(R^2 + \zeta^2)^{\frac{1}{2}}} d\zeta. \quad (23)$$

Recalling the definitions for $\sin \sigma'$ and $\cos \sigma'$ from expression 13, and referring to FIG. 4, it is possible considering the trignometric relationship of the triangles sharing the common angle $\sigma'$ to define $\xi'$ as follows:

$$\zeta' = \frac{R(r \sin(\phi - \theta) + \zeta_s)}{R + r \cos(\phi - \theta)}. \quad (24)$$

This expresses $\xi'$ in terms of the coordinates $(r,\phi)$ and variable $\theta$. Substituting that value for $\xi'$ and the value of D given in equation 14 into equation 23, simplifying and using equation 8, we have expressed Radon's inversion formula which integrates over the fan beam projection coordinates $(\xi,\theta)$ as follows:

$$f(r,\phi) = \frac{1}{4\pi^2} \int_0^{2\pi} g'(\zeta',\theta) \frac{R^2}{(R + r\cos(\phi - \theta))^2} d\theta \quad (25)$$

$$g'(\zeta',\theta) = \lim_{\epsilon \to 0} \int F_\epsilon(\zeta - \zeta') p(\zeta,\theta) \left[ \frac{(1 + \zeta \zeta_s/R^2)}{(1 + \zeta^2/R^2)^{\frac{1}{2}}} \right] d\zeta. \quad (26)$$

It will now be appreciated that the foregoing expressions 24, 25 and 26 provide the basis for a procedure whereby projections taken with a shift in the center of rotation are weighted by a factor which takes into account the shift, the weighting factor being:

$$\frac{(1 + \zeta \zeta_s/R^2)}{(1 + \zeta^2/R^2)^{\frac{1}{2}}}. \quad (27)$$

The so weighted projections are convolved according to the integral of expression 26, and the modified projections $g'(\xi',\theta)$ back projected according to expression 25 to produce the reconstructed image derived from Radon's inversion formula.

In practice, the continuous analytic reconstruction solution set forth in expressions 25 and 26 is implemented in discrete digital sampled data format in high speed digital computers. Such adaptation of the analytic reconstruction requires the introduction of approximations dealing, for example, with sampling considerations with regard to the kernel used to filter the weighted projection data, and the conversion of the sampled filtered projections to continuously sampled filtered projections.

In practicing the invention, the relationships developed above are applied in a digital sampled data system for processing of projections taken in a rotating fan beam system where the center of rotation is shifted from the midline of the fan beam. A weighting function is developed from expression 27 which is a function of system geometry and the magnitude of the shift. Transforming expression 27 to the digitally implemented case where the projection $p(k,\theta_m)$ is a function of the projection bin k and the view angle $\theta_m$, the weighting function for all views as a function of k is defined as:

$$d(k) = \frac{1 + l\zeta_s/R^2}{(1 + l^2/R^2)^{\frac{1}{2}}} \quad (28)$$

where $l = \text{FIX}(k - \text{AXIS})$. The offset AXIS shown in FIG. 2 allows the definition of projection bins beginning at 1 for the first bin. FIX simply indicates that the value in parenthesis is integerized. The projection data $p(k,\theta_m)$ for each view is modified by the weighting function $d(k)$ to provide a weighted projection $g(k,\theta_m)$ as follows:

$$g(k,\theta_m) = d(k) p(k,\theta_m). \quad (29)$$

Several points are noteworthy. First of all, the weighting factor takes account of the shift in the particular geometry utilized as is apparent from expression 26. Secondly, the application of the weighting function is a simple multiplication which can be quickly and efficiently applied to each projection. Finally, as will become apparent from the material to follow, the modified projection sets $g(k,\theta_m)$ can then be convolved individually once per projection and then back projected for each angle to produce the final image.

In performing the convolution in the discrete sampled data environment the kernel in equation 5 has to be sampled. However, in the limit the DC value is undefined. One can show that in the limit as $\epsilon \to 0$, $F_\epsilon(t)$ represents the combination of a derivative and Hilbert transform operations. The derivative operation removes DC components from the projection. Hence, the central value of the kernel has to be set so that the sum of the discrete kernel values is zero. Thus, the discrete values of $F(k)$ are given, within a scale factor used to normalize the final reconstruction, by:

$$F(k) = \begin{cases} \frac{\pi}{4} & \text{if } k = 0 \\ -\frac{1}{\pi k^2} & \text{if } k \text{ odd} \\ 0 & \text{if } k \text{ even} \end{cases} \quad (30)$$

Thus, the convolution of the modified projection set using the desired filter can be expressed as follows:

$$g'(k,\theta_m) = \sum_{k'} F(k - k') g(k',\theta_m). \quad (31)$$

In practice, the convolution is performed using Fast Fourier Transform (FFT) operations incorporating the FFT of the kernel and the FFT of the sampled projection. Because of noise and aliasing the kernel is rolled-off using a suitable window. It turns out that convolutional fan-beam reconstruction algorithms can not be exactly derived if a window is used. However, because the window can be exactly incorporated into convolutional parallel-beam reconstruction algorithms, it has been correctly assumed that the use of a window will not adversely affect the quality of images obtained with the fan-beam algorithm.

Each projection set is convolved independently and stored until the modified convolved projection sets are mapped into pixelized space in accordance with the back projection operation. The actual back projection operation requires all values of the filtered projections over a specified range in contrast to the discrete samples provided by the filtration operation. Typically, the sampled filtered projections are effectively converted to continuously sampled projections using linear interpolation. In the following digital implementation, linear interpolation will be used, appreciating that it is only an approximation to the exact "sinc" interpolation required to restore a band-limited sampled signal. In some applications, higher ordered interpolation schemes might be required.

The back projection of the modified convolved projections into pixelized space $(x_i, y_j)$ can be expressed as:

$$f(x_i, y_j) = \frac{1}{NANG} \sum_{m=1}^{NANG} [f_k g'(k, \theta_m) + (1 - f_k) g'(k+1, \theta_m)] \times \left[ \frac{R^2}{(R + x_i \cos\theta_m + y_j \sin\theta_m)} \right] \quad (32)$$

where $k = FIX(\xi' + AXIS)$, $(1 - f_k) = \xi' + AXIS - k$ and $\xi'$ is given by equation 24. The contribution from the discrete modified projections $g'(k, \theta_m)$ are determined by interpolating between adjacent projection bins, in the present example using linear interpolation. As will become apparent in connection with a discussion of the back projection flow chart, the shift parameter is accounted for in the back projection by appropriately defining the projection bin k as well as the interpolation factor $f_k$ to account for the shift.

In expression 32, the summation signifies a summation of views for all angles from 1 through NANG. Using linear interpolation, a partial contribution $f_k g'(k, \theta_m)$ is determined from the $k^{th}$ modified projection bin for the particular projection $\theta_m$ and the remaining contribution $(1 - f_k) g'(k+1, \theta_m)$ from the $(k+1)^{th}$ modified projection bin. The factor in the continuous analytic solution (expression 25) is defined here as 1/U2:

$$\frac{1}{U2} = \frac{R^2}{(R + r \cos(\phi - \theta))^2}. \quad (33)$$

That factor is transformed into pixelized coordinates to be stated as:

$$\frac{1}{U2} = \frac{R^2}{(R + x_i \cos\theta_m + y_j \sin\theta_m)}. \quad (34)$$

Figure 6:
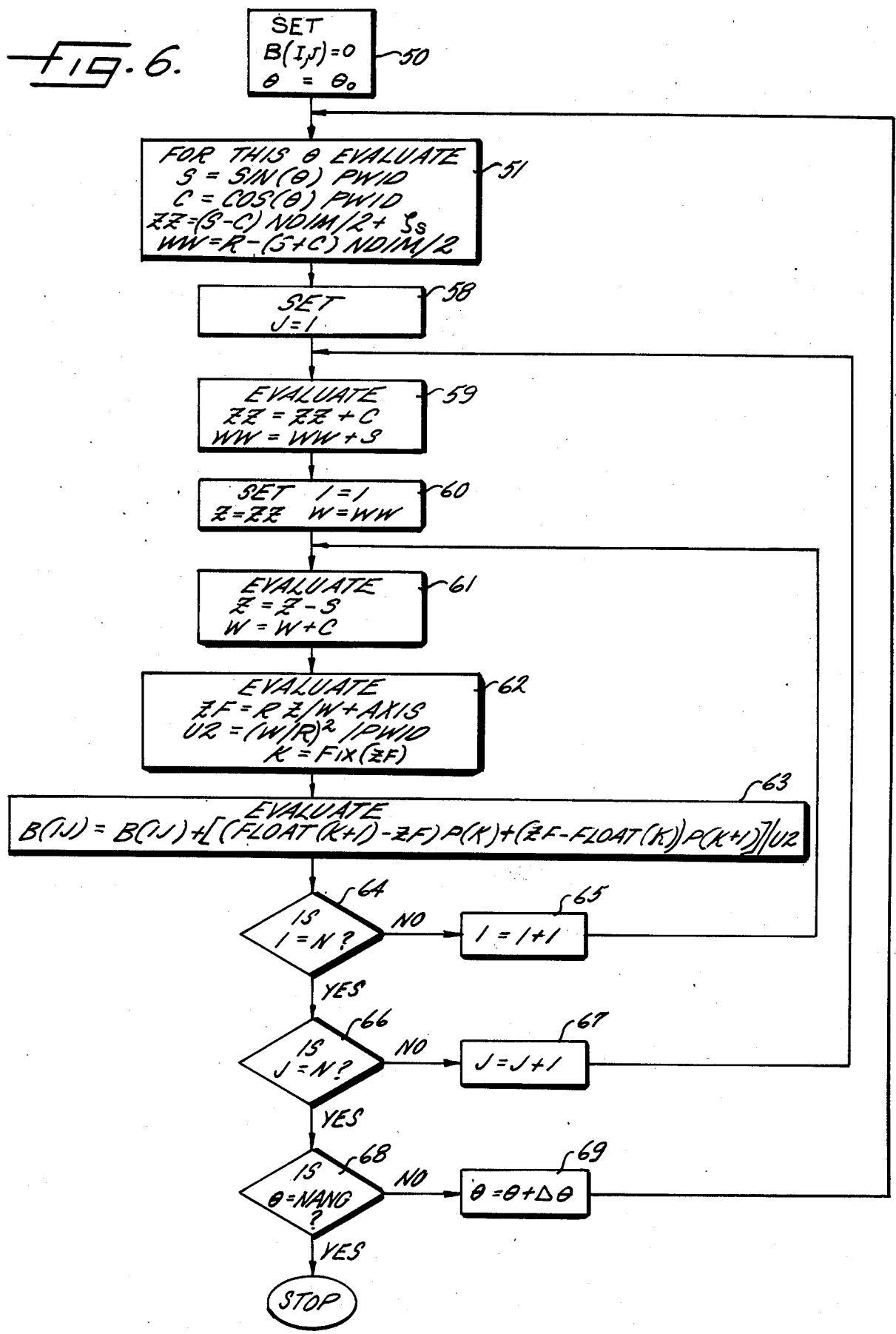
FIG. 6 is a flow diagram illustrating a back projection algorithm for the CT system diagrammed in FIG. 3.

Turning to FIG. 6, there are shown the details of the back projection operation. We believe the illustrated back projection is a particularly efficient implementation, and can be performed using a special purpose hardware processor, as well as in a general purpose computer. The invention is broadly applicable for use with back projection operations of various types.

Referring to FIG. 6, it is seen that the process operates on each projection set in turn (each $\theta$), and for each projection set determines the contribution to each pixel B(I,J) based on linear interpolation between adjacent projection bins as determined by the process. In implementing expression 32, the reconstruction $f(x_i, y_j)$ will be stored in the array B(I,J).

The process is initialized by a step 50 which selects a first projection set and zeros the array B(I,J). In a step 51 various factors are evaluated which allow the Z (vertical) and W (horizontal) (see FIG. 4) coordinates to be incremented by simple sums and differences. The S and C parameters which are evaluated in step 51 can be better appreciated with reference to FIG. 2. It will be recalled that the pixelized space in FIG. 2 is illustrated at an angle $\theta$ with respect to the $\xi$ axis. Thus, any line drawn through a pixel which is either parallel to the $\xi$ axis or parallel to ray R (which in turn is perpendicular to the $\xi$ axis) and intersects the corner of a pixel will form an angle $\theta$ with the pixel edge. A right triangle can be formed with the pixel edge (whose dimension is PWID) and the S parameter of step 51 will be the length of the side opposite the angle $\theta$. Similarly, the C parameter will be the length of the side adjacent the angle $\theta$. In FIG. 2, the pixel 52 shows a triangle having its C side parallel to R, and the pixel 53 illustrates a similar triangle having its C side parallel to the $\xi$ axis.

With that in mind, those skilled in the art will appreciate that S+C represents the length between the projection of two corners of a pixel (such as corners 55, 56) onto the ray R, while S−C represents the length between the projection of the same two corners onto the $\xi$ axis. Multiplying those projections by NDIM/2 as is done in step 51 creates projections onto the ray R and $\xi$ axis equal to the distance from the lower left corner of the pixel (1,1) to the origin. The ZZ and WW values defined in step 51 are the initial values for Z and W parameters shown in FIG. 4. As will become apparent, those values are updated for each pixel to give correct Z and W values for each pixel.

In practicing the invention, the projection onto the $\xi$ axis, identified in step 51 as ZZ, is altered by the value of the shift, by adding the shift $\xi_s$ increment thereto. As will become apparent, by so modifying the back projection geometry with the shift, the previously modified weighted convolved projection sets can be back projected to produce a result wherein both the convolution and back projection are compensated for the shift to produce accurate reconstructions in spite of the shift.

Having now established the initial parameters for the view angle $\theta$, a step 58 is performed to initialize the pixel row index J. A step 59 is then performed to provide ZZ and WW coordinates identifying the particular row of pixels being back projected at that point in the process. As will become apparent, those coordinates are altered only when the back projection switches from one row to another in the pixelized space.

Following the step 59, a step 60 is performed to set the pixel column index I and define temporary parameters Z and W to be incremented as the back projection proceeds along a row of pixels. The Z and W parameters are incremented in step 61 in dependence on the S and C values for the $\theta$ in question. Thus, the result of step 61 is to identify parameters related to Z and W for a particular pixel, in the present instance the first pixel in the back projection array B(1,1). A step 62 is then performed to identify the projection bins which contribute to the pixel in question, and to evaluate the factor U2. More particularly, in evaluating ZF it is seen that the ratio of Z to W is taken then multiplied by R to define the projection of the point in question on the $\xi$ axis. That point is offset by AXIS which as shown in FIG. 2 is simply an offset which allows the definition of projection bins beginning at 1 for the first bin. The step 62 then defines the projection bins which contribute to the pixel by setting bin index K=FIX(ZF).

The inverse of the factor U2 is evaluated by simply squaring the ratio of W over R. As will be appreciated on reference to FIG. 4, that operation yields the inverse of the factor specified in equations 33 and 34. In addition, the factor is divided by PWID in step 62. Processing to this point had been accomplished in units of projection bins. It is now necessary, in building up the image for display, to convert to units of pixel width. In transmission computed tomography, because the attenuation coefficients which are displayed are in units of inverse length, the step 62 uses a division factor of PWID. In emission computed tomography, the units displayed are in terms of counts per unit area; as such, when the back projector of FIG. 6 is used for emission computed tomography, the step 62 would use a division factor of $PWID^2$.

Having identified the projection bin and the U2 factor, the process proceeds to a step 63 which performs the actual back projection. The information previously resident in the memory location for the pixel (I,J), that is B(I,J) is updated by adding an amount linearly interpolated from the K and K+1 projection bins. A proportion of the information in projection bin K, P(K), determined by the difference between the floating point coordinate of projection bin K+1 and ZF is added to a proportion of the information within projection bin K+1, P(K+1), determined by the difference between ZF and the floating point coordinate of projection bin K. That sum is divided by U2, and the result added to B(I,J) to update the information for the pixel in question.

Following the back projection evaluation for the first pixel, a test 64 branches the process to a step 65 which increments the column index I, then returns the process to the step 61 to determine the Z and W coordinates for the next pixel in the row. The evaluation of step 62 is again made following which the back projection operation 63 is accomplished for that pixel. That loop continues to cycle until the test 64 determines that all columns within the first row have been updated, whereupon the process branches to a test 66 which branches to a step 67 to increment the row index J. The process then returns to the step 59 where the temporary ZZ and WW coordinates are updated before processing the second row. In the step 60 the column index I is again set to 1 and Z and W redefined in accordance with the coordinates of the first pixel in the second row. The inner loop including steps 61, 62 and 63 then performs the back projection operation for all pixels in the second row. In like fashion the intermediate loop increments the row index J and the inner loop back projects all pixels in that row until all pixels in the array have been processed. At that point the test 66 branches to another test 68 which in turn branches the operation to a step 69 which increments θ to select the next view for processing. In effect, the xy-coordinate system is rotated to the new view angle θ and the process is repeated for the new view. The process returns to the step 51 and operation proceeds as described above until contributions are made to all pixels for the view then being processed. The operation continues as described until the test 68 determines that all views have been processed whereupon the back projection operation is terminated. The pixelized space at that point contains information back projected from all views such that a display of the information in the pixelized memory produces an image of the cross-section which created the original projections.

Figure 7:
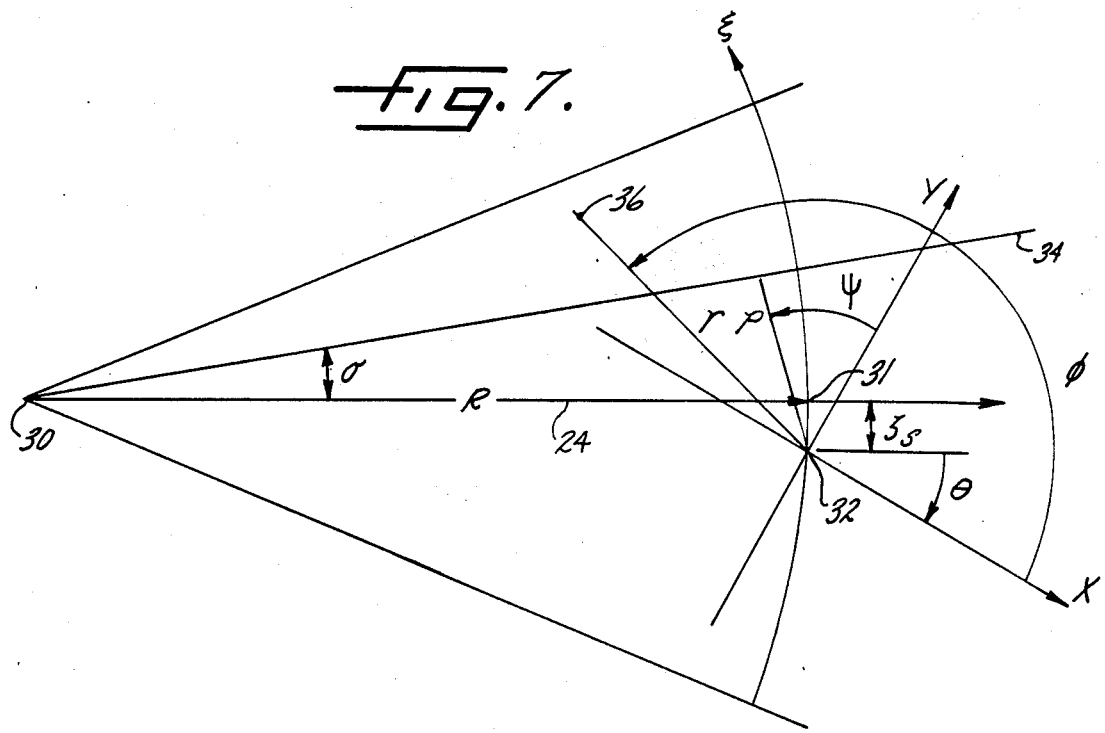
FIG. 7 is a diagram similar to FIG. 3 illustrating a shift in the center of rotation for a curved detector fan beam CT system.

As was noted above, the present invention is not only applicable to the flat detector case characteristic of emission computed tomography, but is also useful in connection with the curved detector case more typically found in transmission computed tomography. Turning to FIG. 7, there is shown the geometry applicable to the curved detector case. It will be appreciated from comparison of FIGS. 7 and 3 that the geometry is the same as that defined with respect to the flat detector except that the $\xi$ axis has been replaced with a $\xi$ axis curved to correspond to the curvature of the detector and having a center ray 24 defining the midline of the fan, and which bisects the fan to intersect the $\xi$ axis at a predetermined point 31. The actual center of rotation is illustrated as the point 32 displaced vertically from the point 31 by a distance $\zeta_s$. The projection bins in FIG. 7 are defined along the $\xi$ axis and are of unit width as described generally in connection with the projection bins in the flat detector case.

A similar derivation to that described in connection with the flat detector can be performed to yield a weighting function and a back projection modification useful in the curved detector case for accommodating the shift in the center of rotation in the reconstruction process. Those skilled in the art can be guided by the foregoing derivation and will appreciate that in the curved detector case the following results apply. More particularly, analogous to the $\xi'$ definition set out in expression 24, in the curved detector case a function $\xi'$ can be defined as follows:

$$\xi' = R \tan^{-1}\left[ \frac{\zeta_s + r\sin(\phi - \theta)}{R + r\cos(\phi - \theta)} \right] . \tag{35}$$

The denominator in the fraction of expression 35 is the same as the W parameter defined in connection with FIG. 4. Similarly, the numerator of the fraction is Z in FIG. 4. In a manner similar to the derivation of expressions 25 and 26, Radon's inversion formula for the curved detector case can be expressed as an integration over the fan beam coordinates $(\xi,\theta)$ as follows:

$$f(r,\phi) = \frac{1}{4\pi^2} \int_0^{2\pi} g'(\xi',\theta)\left[ \frac{R^2}{(R + r\cos(\phi - \theta))^2 + (\zeta_s + r\sin(\phi - \theta))^2} \right] d\theta \tag{36}$$

$$g'(\xi',\theta) = \lim_{\epsilon \to 0} \int F_\epsilon(R\sin(\xi/R - \xi'/R))p(\xi,\theta)[\cos(\xi/R) + \zeta_s/R\sin(\xi/R)]d\xi \tag{37}$$

The form of expression 36 and 37 is very similar to that of expressions 25 and 26. More particularly, the projections are expressed in the desired coordinates, in the present case the curved detector coordinates $(\xi,\theta)$. The filter function $F_\epsilon$ is modified to account for the curvature of the detector. Similarly, the weighting function, the bracketed term in expression 37, is modified to form corresponding to a curved detector. However, that function, as in the previous case accounts for the shift magnitude, and can be individually applied to the projections before convolution and back projection. Finally, the U2 factor set forth in the bracketed term in expression 36 is also somewhat modified.

Applying this continuous analytic solution to the sampled data implementation, a weighting function is defined as follows:

$$e(k) = \cos(l/R) + \xi_s/R \sin(l/R) \tag{38}$$

where $l = \text{FIX}(k - \text{AXIS})$. The weighting function $e(k)$ is applied to the projections to provide weighted projection sets as follows:

$$g(k, \theta_m) = e(k) p(k, \theta_m). \tag{39}$$

The weighted projection sets are then convolved with the filter $$F(k) = \begin{cases} \dfrac{\pi}{4} & \text{if } k = 0 \\ \dfrac{-(1/R^2)}{\pi \sin^2(k/R)} & \text{if } k \text{ odd} \\ 0 & \text{if } k \text{ even} \end{cases} \tag{40}$$

to yield weighted convolved projection sets $g'(k, \theta_m)$ $$g'(k, \theta_m) = \sum_{k'} F(k - k') g(k', \theta_m). \tag{41}$$

The weighted convolved projections are then back projected as follows to give the reconstructed image $$f(x_i, y_j) = \frac{1}{NANG} \sum_{m=1}^{NANG} [f_k g'(k, \theta_m) + (1 - f_k) g'(k+1, \theta_m)] \times \left[ \frac{R^2}{(R + x_i \cos\theta_m + y_j \sin\theta_m)^2 + (\zeta_s - x_i \sin\theta_m + y_j \cos\theta_m)^2} \right] \tag{42}$$

As in the previous case, the contribution of the modified projections $g'(k, \theta_m)$ to the reconstruction $f(x_i, y_j)$ are determined by linearly interpolating between adjacent projection bins.

As in the case of the flat detector, the back projection also takes account in the shift in the center of rotation. The overall process is similar to that of FIG. 6 as described in connection with the flat detector with several exceptions. The exceptions will be noted with reference to FIG. 6 as a means of completely describing the back projection operation. Significantly, the step 51 remains the same and the ZZ parameter is defined to take account of the shift. In the step 62, the ZF parameter is altered in accordance with a curved detector. Rather than using the expression for ZF defined in FIG. 6, ZF in the back projection process for the curved detector is defined as follows:

$$ZF = R \tan^{-1}(Z/W) + \text{AXIS} \tag{43}$$

Similarly, U2 is altered (see expression 42) for the curved detector and is expressed as follows:

$$U2 = \frac{W^2 + Z^2}{R^2(PWID)} \tag{44}$$

With those computational exceptions, the back projection operation proceeds exactly as described in connection with FIG. 6. It will be apparent from the foregoing, that the projection bins, however, are defined along the curved $\xi$ axis of FIG. 7 rather than the perpendicular $\xi$ axis of FIG. 2.

Attention will now be directed to a calibration procedure for estimating the shifted geometric parameters in a fan beam tomographic reconstruction system. The procedure will be described in connection with a flat detector typical of the emission CT case because, as should now be apparent, that is the case in which the shifted center is most likely to occur. However, in principle, the procedure is also applicable to the curved detector case characteristic of transmission CT.

Figure 8:
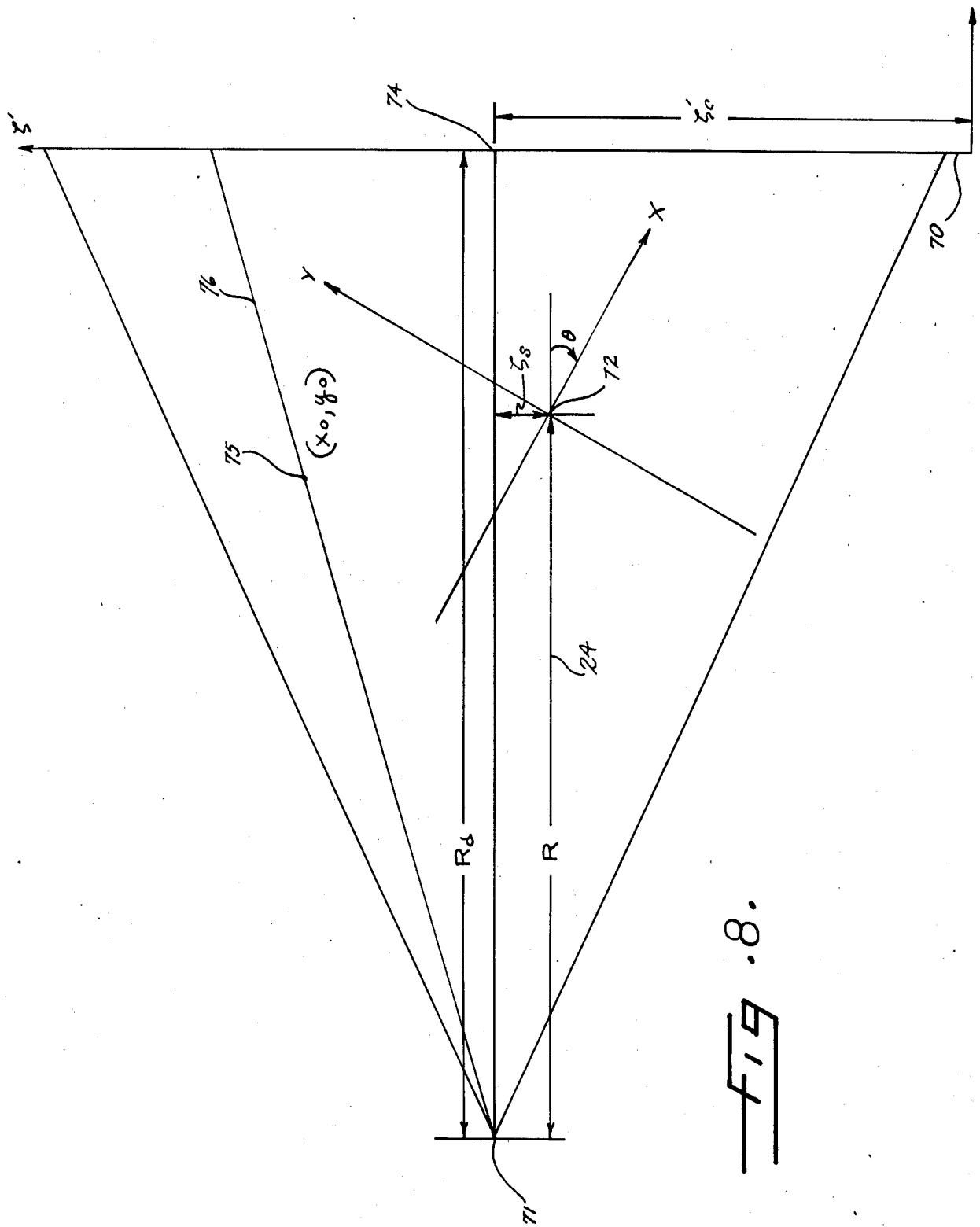
FIG. 8 is a diagram illustrating the shifted geometry and associated parameters for a fan beam ECT system.

Turning to FIG. 8, there is shown a typical geometry for a fan beam tomographic system having a flat detector 70 focused by collimators to a focal point 71, forming a fan with its apex at point 71. The focal length of the collimator, that is, the distance from the apex 71 to the crystal face 70 along a ray which defines the midline of the fan is indicated by $R_d$. It is seen that the center 72 of the rotating xy-coordinate system is displaced from the midline of the fan beam by an amount $\xi_s$. The projection of the apex 71 onto the crystal is indicated at 74, and is at a distance $\xi'_c$ measured from the crystal edge. In the curved detector case, the point 74 would be defined, not by a projection, but by a ray which bisects the fan. The distance from the apex 71 to the center of the rotating coordinate system 72 is indicated as R.

As noted previously, it is difficult with any degree of precision to measure the aforementioned focal lengths and shifts accurately. In accordance with this aspect of the invention, a procedure is provided for accurately estimating those parameters. Accordingly, a point response 75 (in emission CT a point source of radiation and in transmission CT a pin of highly attenuating material) is positioned in the patient aperture at an unknown point such as $(x_o, y_o)$. As with the other parameters, it is also difficult to measure the location of the point source with any degree of precision. It should be noted that in systems having multiple transaxial slice collimators, the point source 75 can actually be a line source extending into the paper so that all slices can be calibrated at the same time. Thus, when point source is used herein it is intended to encompass such a line source made up of a plurality of points.

It is seen in FIG. 8 that the point source 75 defines a ray 76 extending between the focal point 71 and an unknown point on the crystal face. A right triangle can be seen in the figure having as hypotenuse the ray 76, as one side the focal length $R_d$ and as the other side the portion of the crystal face joining those two lines. A similar right triangle can be defined at any point $(x,y)$ on the ray 76. It is therefore possible to define an equation for the ray 76 by taking ratios of corresponding sides of such similar triangles, yielding:

$$(\xi' - \xi_c)(x \cos\theta + y \sin\theta + R)/R_d + x \sin\theta - y \cos\theta + \xi_s = 0 \tag{45}$$

Thus, a projection measured along a ray such as 76 can be specified by its line integral, or stated differently:

$$p_r(\zeta', \theta) = \int\int f(x,y) \delta((\zeta' - \zeta'_c)(x\cos\theta + y\sin\theta + R)/R_d + x\sin\theta - y\cos\theta + \zeta_s) dx dy \tag{46}$$

Substituting the product of Dirac delta functions $\delta(x-x_o)\delta(y-y_o)$ for $f(x,y)$, it is possible to evaluate the projection of a point source 75 by means of the line integral through the point source as follows:

$$p_f(\zeta',\theta) = \delta((\zeta' - \zeta_c') \quad (47)$$

$$(x_o\cos\theta + y_o\sin\theta + R)/R_d + x_o\sin\theta - y_o\cos\theta + \zeta_s)$$

In actual implementation of the calibration procedure, a point source of radiation is used to approximate a delta function. In transmission CT the point source is a pin of highly attenuating material and in emission CT a radioactive substance. The centroid of the projected point source will be approximately located at the $\xi'_i$, which makes the argument in the delta function in expression 47 go to zero. By sampling the centroid $\xi'_i$ of the projection point source for $\theta_i$, $i=1, \ldots, M$, it is possible to minimize a chi-square function:

$$\chi^2(\zeta'_o, R_d, R, \zeta_s, x_o, y_o) = \sum_{i=1}^{M} \left( \zeta'_i - \zeta'_c + \frac{R_d[(x_o + \zeta_s\sin\theta_i)\sin\theta_i - (y_o - \zeta_s\cos\theta_i)\cos\theta_i]}{[(x_o + \zeta_s\sin\theta_i)\cos\theta_i + (y_o - \zeta_s\cos\theta_i)\sin\theta_i + R]} \right)^2 \quad (48)$$

to obtain the parameters $\xi'_c$, $R_d$, $R$, $\xi_s$, $x_o$ and $y_o$.

Minimizing the aforesaid chi-square function requires the use of non-linear estimation techniques. One such technique which is preferred is the Marquardt algorithm described, for example, in the following papers by D. W. Marquardt: Solution of Non-Linear Engineering Models, Chem. Eng. Progr., Vol. 55, pp. 65–70, 1959; An Algorithm for Least Squares Estimation of Non-Linear Parameters, SIAM, Vol. 11, pp. 431–441, 1963. The Marquardt algorithm requires the evaluation of the partial derivatives of the function:

$$f(\xi'_o, R_d, R, \xi_s, x_o, y_o) = \xi'_c - g/h \quad (49)$$

where $$g = R_d[(x_o + \xi_s \sin \theta_i) \sin \theta_i - (y_o - \xi_s \cos \theta_i) \cos \theta_i],$$

$$h = [(x_o + \xi_s \sin \theta_i) \cos \theta_i + (y_o - \xi_s \cos \theta_i) \sin \theta_i + R].$$

The following partial derivatives are those which are used:

$$\frac{\delta f}{\delta \zeta_c'} = 1 \quad (50)$$

$$\frac{\delta f}{\delta R_d} = \frac{-g}{R_d h} \quad (51)$$

$$\frac{\delta f}{\delta R} = \frac{g}{h^2} \quad (52)$$

$$\frac{\delta f}{\delta \zeta_s} = \frac{-R_d}{h} \quad (53)$$

$$\frac{\delta f}{\delta x_o} = \frac{-R_d[y_o - \cos\theta_i\zeta_s + \sin\theta_i R]}{h^2} \quad (54)$$

$$\frac{\delta f}{\delta y_o} = \frac{R_d[x_o + \zeta_s\sin\theta_i + R\cos\theta_i]}{h^2} \quad (55)$$

Thus, the values of the geometric parameters are varied, and the aforementioned partial derivatives evaluated according to the Marquardt algorithm to minimize the chi-square function specified in expression 48. It is seen that $\xi'_i$ within that function is the centroid of the projected point source which is compared with the line integral of the ray. Thus, by using the Marquardt algorithm and varying the geometric parameters, one is effectively evaluating the line integral which will come nearest the measured centroid of the projected point source.

Based on the theory discussed above, in practicing the invention to estimate the geometric parameters of a fan beam tomographic system, a point response is positioned within the scan circle at an unknown point, and the detector rotated about its center to take a set of projections. Those projections are stored for later comparison, and the centroid for each projection is determined. By using simple measurements, past experience or best estimates, an initial value is assigned to each of the geometric parameters $\xi'_c$, $R_d$, $R$, $\xi_s$, $x_o$ and $y_o$. Those parameters are then used to define a projection coordinate for the ray passing through the point source, for each view or projection. A function is established relating the centroid for each angle (determined from the projection information) to the geometric factors and an estimated position of the point source. The geometric parameters are systematically and iteratively varied to minimize the difference between the measured and calculated information. The set of geometric parameters which produce the minimum difference between the centroid of the projections and the projection point which is a function of the geometric parameters, are then utilized in the reconstruction process.

It can be found in practicing the invention that many local minimums are present which are not the true minimum being sought. To avoid settling on a local minimum, it is useful to start with initial estimates which are as accurate as possible, obtained from measurements or simple experiments. It has also been found useful to vary only certain of the parameters at first to increase their precision before varying others. It has been found useful to vary only $\xi_s$ initially, holding the other geometric parameters constant, then to progressively include variations in the other parameters in the following order: $x_o$, $y_o$, $\xi'_c$, $R$, and $R_d$.

The method of the invention, described in detail above, can be practiced in concert with the reconstruction computer 16 (see FIG. 1) which is an element of the CT system. More particularly, the computer 16 can be programmed to carry out the steps of the method, and when properly programmed by those skilled in the art based on the foregoing disclosure, comprises an apparatus for estimating or compensating for the shift of the center of rotation in performing computed tomographic reconstructions.

It will now be appreciated that what has been provided is a simple and efficient method and means for determining and correcting for shifts in the center of rotation of a rotating fan beam computed tomographic system. A calibration procedure is provided in which a point source is positioned to define a ray for each view passing through the point source. A set of projections is taken, a projection point for each of the aforementioned rays is set up, and iteratively compared to the projection sets to minimize the error therebetween, yielding accurate estimates for the shifted parameters. In the reconstruction operation, a weighting factor is determined, dependent on the magnitude of the shift in the center of rotation, and is applied to each term of each projection in a first operation to produce weighted projection sets. The weighted projection sets are then convolved in the usual way to produce modified projection sets ready for back projection. The back projection operation maps the modified projection sets into pixelized space while at the same time again accommodating for the shift in the center of rotation. As a result, convolutional back projection techniques can be used to produce accurate images in computed tomographic systems even though the center of rotation has shifted from that normally expected by conventional reconstruction algorithms.

We claim as our invention:

1. In a fan beam computed tomographic system having a detector system for taking a plurality of projections at a plurality of angles, each projection defining a plurality of projection bins, the computed tomographic system having a given center of rotation which is shifted from the midline of the fan by a predetermined shift distance, a method of compensating for the shift in performing the computed tomographic reconstruction comprising the steps of, producing a non-constant series of weighting functions, one for each projection bin in the fan beam projection sets and which are dependent on the detector geometry and the magnitude of the shift; weighting the information in each projection bin in the fan beam projection sets with its associated weighting function to produce corrected fan beam projection sets, convolving the corrected fan beam projection sets with a filter function to produce convolved corrected fan beam projection sets, setting up a coordinate system in pixelized space located with respect to said pixelized space to take account of the shift, and back projecting the convolved corrected fan beam projection sets into the pixelized space using said coordinate system to produce a CT image corrected for the shift.

2. The method of claim 1 in which said detector is a flat detector and the midline of the fan is on a ray through the apex of the fan and normal to the detector.

3. The method of claim 1 in which said detector is a curved detector and the midline of the fan bisects the fan.

4. The method of claim 1 in which the step of setting up a coordinate system includes setting up a rotating coordinate system in pixelized space having a center of rotation corresponding to said given center of rotation.

5. The method of claim 1 in which the computed tomographic system includes at least a source of penetrating radiation disposed for rotation about the given center of rotation to take the projections.

6. The method of claim 1 in which the computed tomographic system includes a gamma camera and a converging collimator disposed for rotation about the given center of rotation to take the projections.

7. In a fan beam computed tomographic system having a detector system for taking a plurality of projections at a plurality of angles, each projection defining a plurality of projection bins, the computed tomographic system having a given center of rotation which is shifted from the midline of the fan by a predetermined shift distance, an improved apparatus for compensating for the shift in performing the computed tomographic reconstruction comprising means for producing a non-constant series of weighting functions, one for each projection bin in the fan beam projection sets and which are dependent on the detector geometry and the magnitude of the shift; means for weighting the information in each projection bin in the fan beam projection sets with its associated weighting function to produce corrected fan beam projection sets, means for convolving the corrected fan beam projection sets with a filter function to produce convolved corrected fan beam projection sets, means for setting up a coordinate system in pixelized space located with respect to said pixelized space to take account of the shift, and means for back projecting the convolved corrected fan projection sets into the pixelized space using said coordinate system to produce a CT image corrected for the shift.

8. The apparatus of claim 7 in which said detector is a flat detector and the midline of the fan is on a ray through the apex of the fan and normal to the detector.

9. The apparatus of claim 7 in which said detector is a curved detector and the midline of the fan bisects the fan.

10. The apparatus of claim 7 in which the step of setting up a coordinate system includes setting up a rotating coordinate system in pixelized space having a center of rotation corresponding to said given center of rotation.

11. The apparatus of claim 7 in which the computed tomographic system includes at least a source of penetrating radiation disposed for rotation about the given center of rotation to take the projections.

12. The apparatus of claim 7 in which the computed tomographic system includes a gamma camera and a converging collimator disposed for rotation about the given center of rotation to take the projections.

13. In a fan beam computed tomographic reconstruction system having a detector system for taking a plurality of projections at a plurality of angles, and defining a set of geometric parameters including a distance between the apex of the fan and the detector, a distance between the apex of the fan and the center of rotation of the detector, a position of a point on the detector defined by the midline of the fan, and a center of rotation shifted with respect to said projection, a method of estimating said geometric parameters comprising the steps of, providing a point response at an unknown point for sensing by the detector, taking a set of projections of the point response at a plurality of angles by rotating the detector about its center of rotation, determining the centroid of each projection, establishing a function relating the centroid for each angle to said geometric factors and an estimated position of said point, determining the error between the centroid of the point response determined from the projection information and said function, and iteratively determining the set of geometric parameters which minimize said error for use in the reconstruction process.

14. The method of claim 13 in which the point response is a point source of radiation for sensing by an emission computed tomographic system.

15. The method of claim 13 wherein said point response is a pin of highly attenuating material for sensing by a transmission computed tomographic system.

16. The method of claim 13 in which the detector is flat, and the point on the detector defined by the midline of the fan is established by the ray through the apex of the fan which is normal to the detector.

17. The method of claim 13 in which the detector is curved, and the point on the detector defined by the midline of the fan is established by the ray which bisects the fan.

* * * * *

UNITED STATES PATENT AND TRADEMARK OFFICE
CERTIFICATE OF CORRECTION

PATENT NO. : 4,703,424

DATED : October 27, 1987

INVENTOR(S) : Grant T. Gullberg and Carl R. Crawford

It is certified that error appears in the above-identified patent and that said Letters Patent is hereby corrected as shown below:

In the Specification:

Column 5, line 33, change "$(\xi,\theta)$" to --$(\zeta,\theta)$--.
Column 5, line 34, change "$(\xi,\theta)$" to --$(\zeta,\theta)$--.
Column 5, line 46, change "$d\xi$" to --$d\zeta$--.
Column 5, line 51, change "$\xi$" to --$\zeta$--.

Column 6, line 11, change "$\xi$" to --$\zeta$--.
Column 6, line 13, change "$(\tau,u)$" to --$(\tau,\zeta)$--.
Column 6, line 16, change "$\xi$" to --$\zeta$--.
Column 6, line 17, change "$\xi_s$" to --$\zeta_s$--.

Column 7, line 8, change "$(\xi,\theta)$" to --$(\zeta,\theta)$--.
Column 7, line 17, change "$(\xi,\theta)$" to --$(\zeta,\theta)$--.
Column 7, line 25, change "$\xi$" to --$\zeta$--.
Column 7, line 60, (Equation 13, first line),
    change "$\xi_s$" to --$\zeta_s$--.

Column 7, line 61, (Equation 13, second line),
    change $\sigma$ to $\sigma'$.
Column 7, line 67, (Equation 14), change "$\xi_s$" to --$\zeta_s$--, both occurrences.

Column 8, line 53, change "$(\xi-\xi')$" to --$(\zeta-\zeta')$--
    and change "$\xi'$" to --$\zeta'$--.
Column 8, line 55, change "$\xi=R$" to --$\zeta=R$--.
Column 8, line 56, change "$\xi$" to --$\zeta$-- and
    change "$\xi'$" to --$\zeta'$--.
Column 8, line 57, change "$\xi$" to --$\zeta$--.

Column 9, line 2, change "$(\xi-\xi')$" to --$(\zeta-\zeta')$--.
Column 9, line 10, change "$(\xi,\theta)$" to --$(\zeta,\theta)$--.

UNITED STATES PATENT AND TRADEMARK OFFICE
CERTIFICATE OF CORRECTION

PATENT NO. : 4,703,424

DATED : October 27, 1987

INVENTOR(S) : Grant T. Gullberg and Carl R. Crawford

It is certified that error appears in the above-identified patent and that said Letters Patent is hereby corrected as shown below:

Column 9, line 18, change "$\xi'$" to --$\zeta'$--.
Column 9, line 25, change "$\xi'$" to --$\zeta'$--.
Column 9, line 26, change "$\xi'$" to --$\zeta'$--.
Column 9, line 30, change "$(\xi,\theta)$" to --$(\zeta,\theta)$--.
Column 9, line 51, change "$(\xi,'\theta)$" to --$(\zeta,'\theta)$--.

Column 11, line 28, change "$\xi'$" to --$\zeta'$--, both occurrences.
Column 11, line 29, change "$\xi'$" to --$\zeta'$--.

Column 12, line 11, change "$\xi$" to --$\zeta$--.
Column 12, line 13, change "$\xi$" to --$\zeta$--.
Column 12, line 14, change "$\xi$" to --$\zeta$--.
Column 12, line 22, change "$\xi$" to --$\zeta$--.
Column 12, line 28, change "$\xi$" to --$\zeta$--.
Column 12, line 29, change "$\xi$" to --$\zeta$--.
Column 12, line 36, change "$\xi$" to --$\zeta$--.
Column 12, line 38, change "$\xi_s$" to --$\zeta_s$--.
Column 12, line 66, change "$\xi$" to --$\zeta$--.

Column 14, line 19, change "$\xi$" to --$\zeta$--, both occurrences.
Column 14, line 25, change "$\xi_s$" to --$\zeta_s$--.

Column 14, line 37, change "$\xi'$" to --$\zeta'$--.

Column 15, line 10, (Equation 38) change "$\xi_s$" to --$\zeta_s$--.

Column 16, line 5, after the word "perpendicular", change "$\xi$" to --$\zeta$--.

Column 16, line 24, change "$\xi_s$" to --$\zeta_s$--.

Column 16, line 26, change "$\xi'_c$" to --$\zeta_c$--.

UNITED STATES PATENT AND TRADEMARK OFFICE
CERTIFICATE OF CORRECTION

PATENT NO. : 4,703,424

DATED : October 27, 1987

INVENTOR(S) : Grant T. Gullberg and Carl R. Crawford

It is certified that error appears in the above-identified patent and that said Letters Patent is hereby corrected as shown below:

Column 16, line 60, (Equation 45, first line), change "$(\xi'-\xi_c)$" to --$\zeta'-\zeta_c$--.

Column 17, line 15, change "$\xi'_i$" to --$\zeta'_i$--.
Column 17, line 17, change "$\xi'_i$" to --$\zeta'_i$--.
Column 17, line 24, change "$\xi'_c$" to --$\zeta'_c$-- and change "$\xi_s$" to --$\zeta_s$--.

Column 17, line 36, (Equation 49, three occurrences), change "$\xi$" to --$\zeta$--.

Column 17, line 40, change "$\xi$" to --$\zeta$--, both occurrences in the equation.

Column 17, line 42, change "$\xi$" to --$\zeta$--, both occurrences in the equation.

Column 17, line 60, (Equation 54, top line), change "$R_d$" to -- $-R_d$ --.

Column 17, line 67, change "$\xi'_i$" to --$\zeta'_i$--.

Column 18, line 15, change "$\xi'_c$" to --$\zeta'_c$-- and change "$\xi_s$" to --$\zeta_s$--.

Column 18, line 43, change "$\xi_s$" to --$\zeta_s$--.

Column 18, line 46, change "$\xi'_c$" to --$\zeta'_c$--.

Signed and Sealed this

Twenty-ninth Day of March, 1988

*Attest:*

DONALD J. QUIGG

*Attesting Officer*     *Commissioner of Patents and Trademarks*